(12) United States Patent
Lin et al.

(10) Patent No.: US 10,488,477 B2
(45) Date of Patent: Nov. 26, 2019

(54) PARTIALLY FOLDED GRADIENT COIL UNIT

(71) Applicant: General Electric Company, Schenectady, NY (US)

(72) Inventors: Jian Lin, Shanghai (CN); Jean-Baptiste Mathieu, Florence, SC (US); Yihe Hua, Wuxi (CN); Seung-Kyun Lee, Cohoes, NY (US); Dominic Michael Graziani, Loudonville, NY (US)

(73) Assignee: General Electric Company, Schenectady, NY (US)

( * ) Notice: Subject to any disclaimer, the term of this patent is extended or adjusted under 35 U.S.C. 154(b) by 53 days.

(21) Appl. No.: 15/571,585

(22) PCT Filed: Apr. 28, 2016

(86) PCT No.: PCT/US2016/029679
§ 371 (c)(1),
(2) Date: Nov. 3, 2017

(87) PCT Pub. No.: WO2016/178887
PCT Pub. Date: Nov. 10, 2016

(65) Prior Publication Data
US 2018/0156880 A1    Jun. 7, 2018

(30) Foreign Application Priority Data

May 4, 2015 (CN) .......................... 2015 1 0221241

(51) Int. Cl.
*G01R 33/385* (2006.01)
*A61N 1/08* (2006.01)
*A61B 5/055* (2006.01)

(52) U.S. Cl.
CPC ......... *G01R 33/3856* (2013.01); *A61N 1/086* (2017.08); *G01R 33/385* (2013.01); *G01R 33/3858* (2013.01); *A61B 5/055* (2013.01)

(58) Field of Classification Search
CPC .............. G01R 33/3856; G01R 33/385; G01R 33/3858
See application file for complete search history.

(56) References Cited

U.S. PATENT DOCUMENTS

| 4,769,623 A | 9/1988 | Marsing et al. |
| 5,343,148 A | 8/1994 | Westphal et al. |

(Continued)

FOREIGN PATENT DOCUMENTS

| CN | 1766669 A | 5/2006 |
| CN | 101876692 A | 11/2010 |
| GB | 2 265 986 A | 10/1993 |

OTHER PUBLICATIONS

Petropoulos, L. S., and Morich, M. A., "Novel Gradient Coil Set with Canceled Net Thrust Force for Nuclear Magnetic Resonance Applications," IEEE Transactions on Magnetics, vol. 31, Issue 6, pp. 3536-3538 (Nov. 1995) (Abstract from https://ieeexplore.ieee.org/document/489561, last viewed Dec. 3, 2018).

(Continued)

*Primary Examiner* — G. M. A Hyder

(57) ABSTRACT

A gradient coil unit having a peripheral surface enclosing a magnetic gradient axis, and a middle plane substantially perpendicular to the magnetic gradient axis at a middle portion of the gradient coil unit, comprising at least one folded coil which comprises a first set of curved conductors disposed on a first curved surface; a second set of curved conductors disposed on a second curved surface outside the first curved surface and substantially overlapping the first set of curved conductors; and a set of connecting conductors connecting selected curved conductors in the first set with (Continued)

selected curved conductors in the second set; wherein the set of connecting conductors is located at a first side of the middle plane.

14 Claims, 11 Drawing Sheets

(56) References Cited

U.S. PATENT DOCUMENTS

| | | | |
|---|---|---|---|
| 5,349,318 A * | 9/1994 | Inoue | G01R 33/4215 |
| | | | 324/318 |
| 5,561,371 A | 10/1996 | Schenck | |
| 5,646,532 A | 7/1997 | Knuettel et al. | |
| 5,666,054 A | 9/1997 | Westphal | |
| 6,023,166 A | 2/2000 | Eydelman | |
| RE36,881 E | 9/2000 | Muller | |
| 6,297,635 B1 * | 10/2001 | Arz | G01R 33/385 |
| | | | 324/318 |
| 6,975,115 B1 | 12/2005 | Fujita et al. | |
| 7,282,915 B2 | 10/2007 | Giaquinto et al. | |
| 7,526,330 B1 | 4/2009 | Randell et al. | |
| 7,548,064 B1 * | 6/2009 | Wang | G01R 33/3858 |
| | | | 324/309 |
| 7,663,367 B2 | 2/2010 | Wiggins | |
| 7,932,722 B2 | 4/2011 | Amm et al. | |
| 8,571,632 B2 | 10/2013 | Piron et al. | |
| 2006/0113996 A1 | 6/2006 | Feenan | |
| 2007/0188173 A1 | 8/2007 | Overweg | |
| 2008/0094064 A1 | 4/2008 | Eberler et al. | |
| 2010/0244836 A1 * | 9/2010 | Hollis | G01R 33/385 |
| | | | 324/318 |
| 2014/0184372 A1 | 7/2014 | Mathieu et al. | |
| 2017/0038444 A1 * | 2/2017 | Seeber | G01R 33/3858 |

OTHER PUBLICATIONS

First Office Action and Search issued in connection with corresponding CN Application No. 201510221241.3 dated Jul. 2, 2018 (English Translation Unavailable) 8 pages.

International Search Report and Written Opinion for International Application No. PCT/US2016/029679 dated Jul. 29, 2016. 12 pages.

\* cited by examiner

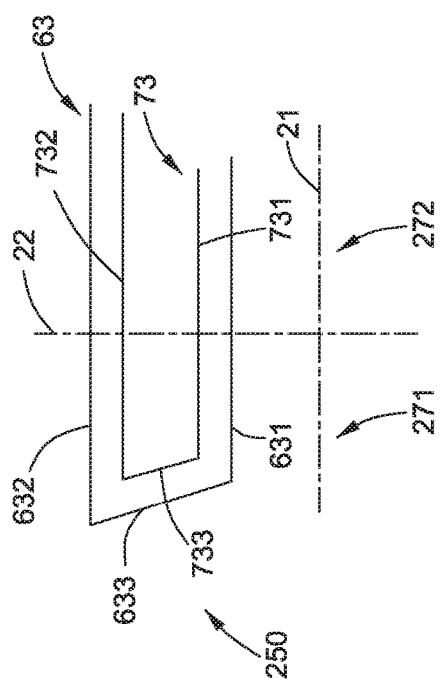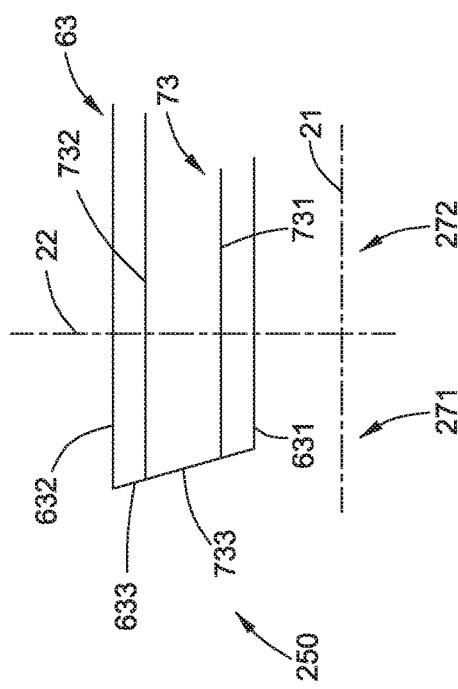

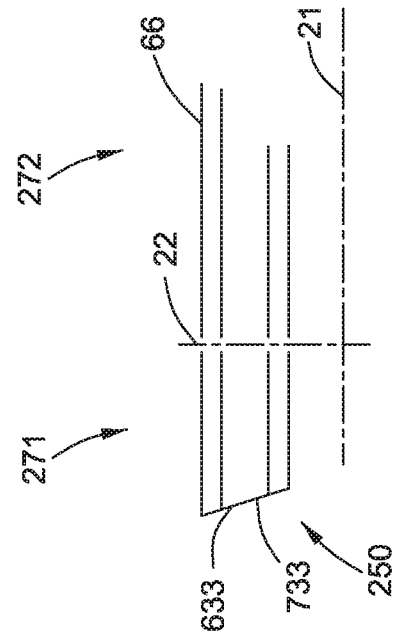
FIG. 10
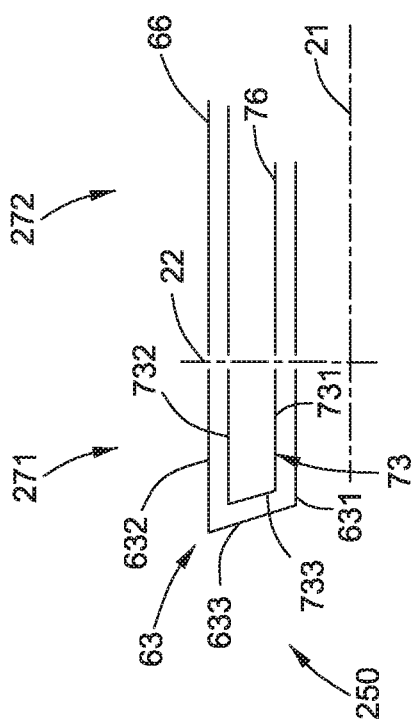
FIG. 11
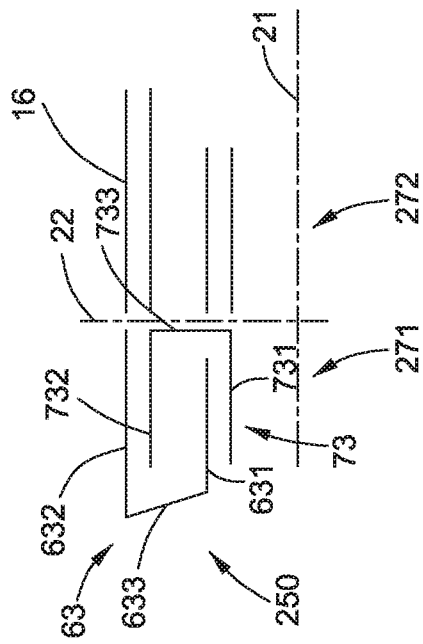
FIG. 12
FIG. 13

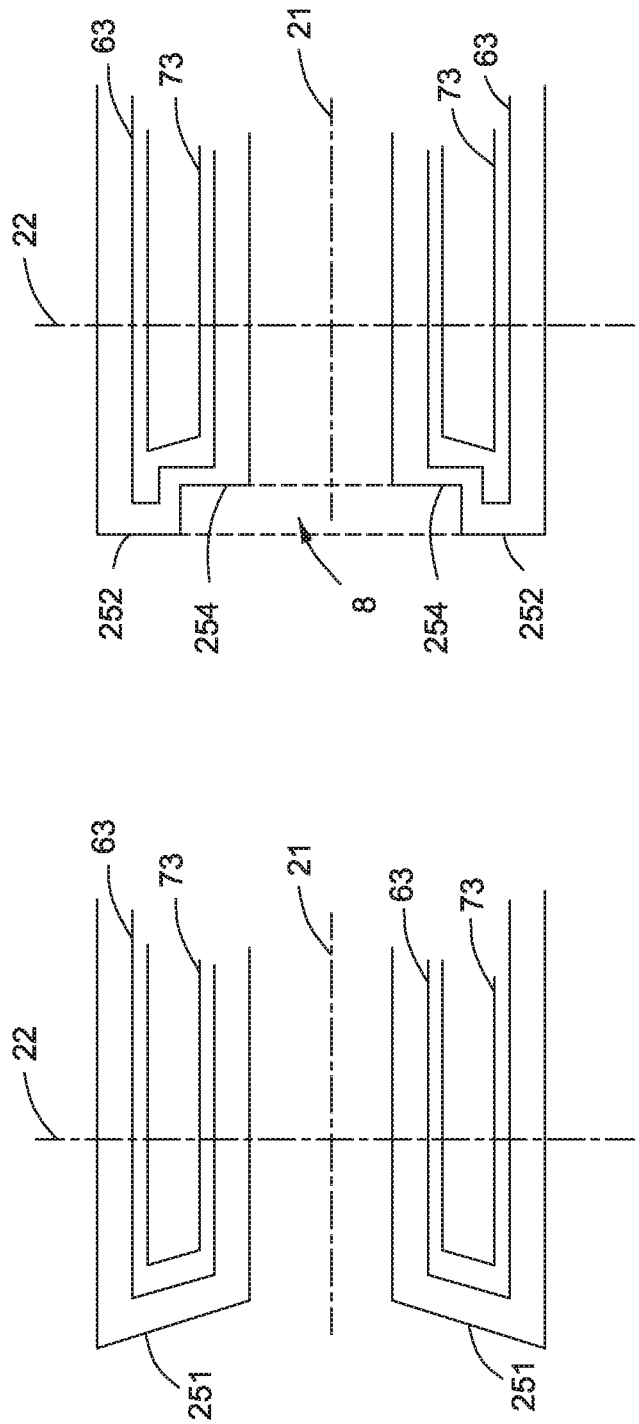

PARTIALLY FOLDED GRADIENT COIL UNIT

CROSS-REFERENCE TO RELATED APPLICATIONS

This is a national stage application under 35 U.S.C. § 371(c) of PCT Patent Application No. PCT/US2016/029679, filed on Apr. 28, 2016, which claims priority to Chinese Patent Application No. 201510221241.3, filed on May 4, 2015, the disclosures of which are incorporated herein by reference in their entireties.

BACKGROUND

Embodiments of the present disclosure relate generally to gradient coil units, and more particularly to partially folded gradient coil units.

Magnetic resonance imaging (MRI) is a medical imaging technique used in radiology to investigate anatomy and physiology of the body. An MRI system may cause anxiety because the patient must lie quietly inside a narrow tube, and a long MRI system may increase discomfort of claustrophobia patients.

In conventional methods, a length of the MRI system may be shortened by folding some coils at both ends of the MRI system, which greatly compresses internal space of the gradient coil, thus increasing complexity of design and manufacturing, especially for a service end of the MRI system which usually needs more space for receiving elements such as cooling channels and thermal sensors.

In addition, folded coils may generate more heat when working, which will cause a problem of overheating.

Therefore, it is desirable to provide new gradient coil units to solve the above-mentioned problems.

BRIEF DESCRIPTION

The following summary presents a simplified summary in order to provide a basic understanding of some aspects of the system and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

One aspect of the present disclosure provides a gradient coil unit having a peripheral surface enclosing a magnetic gradient axis, and a middle plane substantially perpendicular to the magnetic gradient axis at a middle portion of the gradient coil unit. The gradient coil unit comprises at least one folded coil, which comprises a first set of curved conductors, a second set of curved conductors and a set of connecting conductors connecting selected curved conductors in the first set with selected curved conductors in the second set. The first set of curved conductors is disposed on a first curved surface. The second set of curved conductors is disposed on a second curved surface outside the first curved surface and the second set of curved conductors substantially overlaps the first set of curved conductors. The set of connecting conductors is located at a first side of the middle plane.

Another aspect of the present disclosure provides an apparatus having a peripheral surface enclosing a magnetic gradient axis, and a middle plane substantially perpendicular to the magnetic gradient axis at a middle portion of the apparatus. The apparatus comprises an X gradient coil unit and a Y gradient coil unit. The Y gradient coil unit is substantially concentric with X gradient coil unit and at least a part of which is sleeved by the X gradient coil unit. Each of the X and Y gradient coil unit comprises at least one folded coil which comprises a first set of curved conductors, a second set of curved conductors and a set of connecting conductors connecting selected curved conductors in the first set with selected curved conductors in the second set. The first set of curved conductors is disposed on a first curved surface. The second set of curved conductors is disposed on a second curved surface outside the first curved surface and the second set of curved conductors substantially overlaps the first set of curved conductors. The set of connecting conductors is located at a first side of the middle plane.

DRAWINGS

These and other features, aspects, and advantages of the present disclosure will become better understood when the following detailed description is read with reference to the accompanying drawings in which like characters represent like parts throughout the drawings, wherein:

FIG. 8 shows a relationship between the X and Y gradient coil units in accordance with an exemplary embodiment of the present disclosure.

FIG. 9 shows a relationship between the X and Y gradient coil units in accordance with another exemplary embodiment of the present disclosure.

FIG. 10 shows a relationship between the X and Y gradient coil units in accordance with another exemplary embodiment of the present disclosure.

FIG. 11 shows a relationship between the X and Y gradient coil units in accordance with another exemplary embodiment of the present disclosure.

FIG. 12 shows a relationship between the X and Y gradient coil units in accordance with another exemplary embodiment of the present disclosure.

FIG. 13 shows a relationship between the X and Y gradient coil units in accordance with another exemplary embodiment of the present disclosure.

FIG. 16 shows a structure of a first end surface of the apparatus in accordance with an exemplary embodiment of the present disclosure; and FIG. 17 shows a structure of the first end surface of the apparatus in accordance with another exemplary embodiment of the present disclosure.

DETAILED DESCRIPTION

Figure 1:
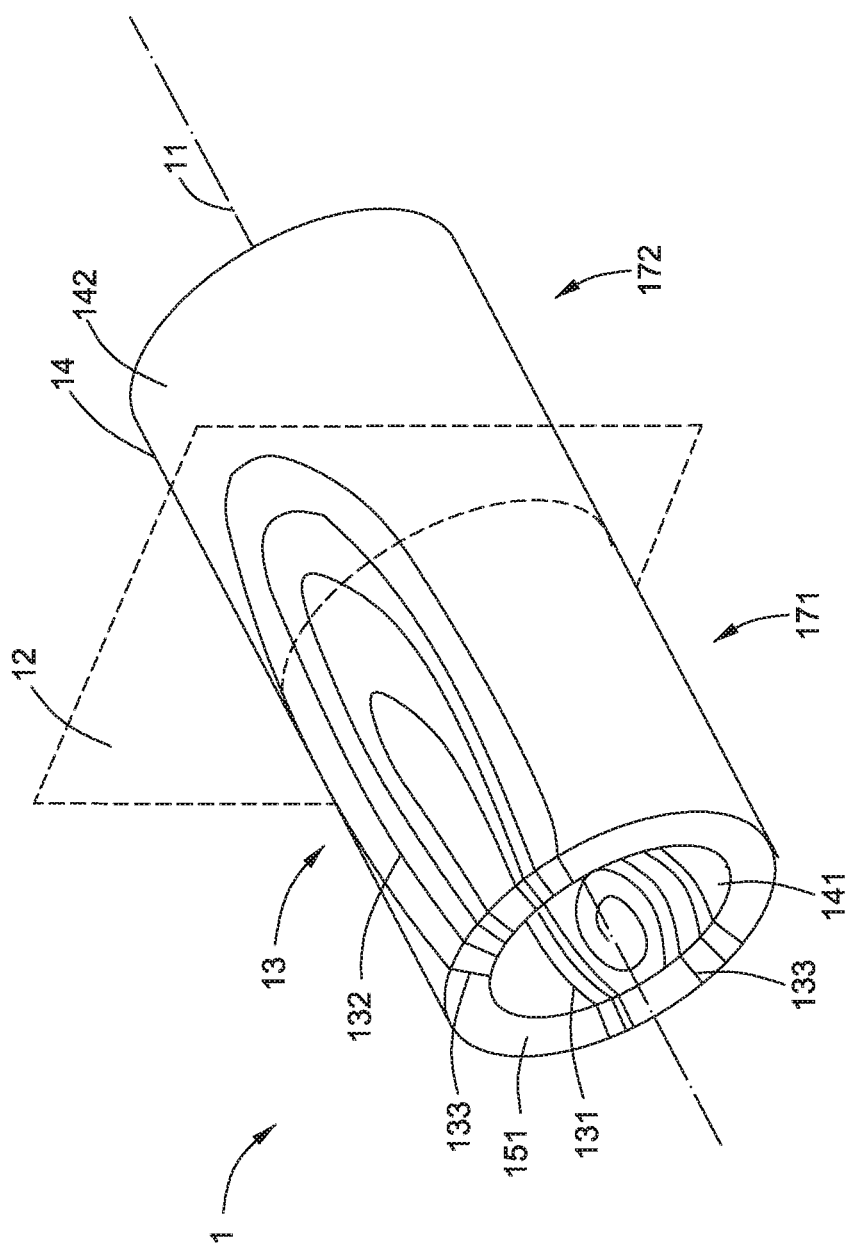
FIG. 1 is a sketch view of a gradient coil unit including a folded coil in accordance with an exemplary embodiment of the present disclosure.

In an effort to provide a concise description of these embodiments, not all features of an actual implementation are described in one or more specific embodiments. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of the present disclosure.

Unless defined otherwise, technical and scientific terms used herein have the same meaning as is commonly understood by one of ordinary skill in the art to which the present disclosure belongs. The terms "first," "second," "third," "fourth," and the like, as used herein do not denote any order, quantity, or importance, but rather are used to distinguish one element from another. Also, the terms "a" and "an" do not denote a limitation of quantity, but rather denote the presence of at least one of the referenced items. The term "or" is meant to be inclusive and mean either any, several, or all of the listed items. The use of "including," "comprising," or "having," and variations thereof herein are meant to encompass the items listed thereafter and equivalents thereof as well as additional items.

As used herein, the terms "may," "can," "may be," and "can be" indicate a possibility of an occurrence within a set of circumstances; a possession of a specified property, characteristic or function; and/or qualify another verb by expressing one or more of an ability, capability, or possibility associated with the qualified verb. Accordingly, usage of "may," "can," "may be," and "can be" indicate that a modified term is apparently appropriate, capable, or suitable for an indicated capacity, function, or usage, while taking into account that in some circumstances, the modified term may sometimes not be appropriate, capable, or suitable. For example, in some circumstances, an event or capacity may be expected, while in other circumstances, the event or capacity may not occur. This distinction is captured by the terms "may," "can," "may be," and "can be".

Embodiments of the present disclosure refer to gradient coil units applicable in a magnetic resonance imaging (MRI) system. Gradient coil units are important elements in the MRI system, which are configured to generate predefined magnetic fields. Structures of the gradient coil units largely determine performance and manufacturing complexity of the MRI system.

An MRI system usually comprises three types of gradient coil units, i.e. X, Y and Z gradient coil units, configured to generate gradients in three directions respectively. The gradient coil units discussed herein are generally used as the X and Y gradient coil units, which are similar in structure.

Figure 3:
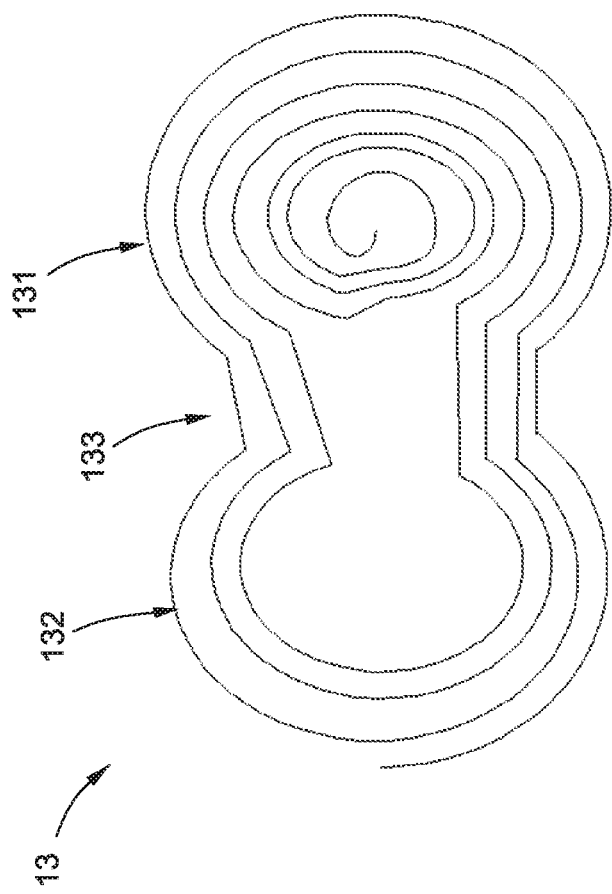
FIG. 3 shows an unfolded status of an exemplary folded coil for gradient coil units of the present disclosure.

Referring to FIG. 1 and FIG. 3, a gradient coil unit 1 has a peripheral surface 14 enclosing a magnetic gradient axis 11. A middle plane 12 substantially perpendicular to the magnetic gradient axis 11 at a middle portion of the gradient coil unit 1 divides the gradient coil unit 1 into two side parts, a first side 171 and a second side 172. The gradient coil unit 1 comprises at least one folded coil 13, which is arranged close to the peripheral surface 14. The folded coil 13 comprises a first set of curved conductors 131, a second set of curved conductors 132 and a set of connecting conductors 133 configured to connect selected curved conductors in the first set 131 with selected curved conductors in the second set 132. As shown in FIG. 1, the first set of curved conductors 131 is disposed on a first curved surface 141. The second set of curved conductors 132 is disposed on a second curved surface 142 outside the first curved surface 141, and substantially overlaps the first set of curved connectors 131. The gradient coil unit 1 folds only at the first side 171 but not at the second side 172 so as to spare space for other elements at the second side 172, and thus the set of connecting conductors 133 extending between the first curved surface 141 and the second curved surface 142 is located at the first side 171, not at the second side 172. This design not only shortens the length of the gradient coil unit 1 in some degrees but also decreases the manufacturing complexity. In some embodiments, the gradient coil unit 1 may comprise a plurality of folded coils 13, and the sets of connecting conductors 133 are all located at the first side 171.

In some embodiments, the gradient coil unit 1 is in a shape of cylinder, and thus the peripheral surface 14 is a cylindrical surface. The first curved surface 141 and the second curved surface 142 are cylindrical and concentric with each other relative to the magnetic gradient axis 11. The second curved surface 142 may be integrated with the peripheral surface 14.

Referring to FIG. 1, the gradient coil unit 1 comprises two folded coils 13 symmetric about the magnetic gradient axis 11. Each of the folded coils 13 extends across the middle plane 12 from the first side 171 to the second side 172. More specifically, the first set of the curved conductors 131 and the second set of the curved conductors 132 both extend across the middle plane 12. The sets of connecting conductor 133 of both two folded coils 13 are located at a first end surface 151 of the gradient coil unit 1.

Figure 2:
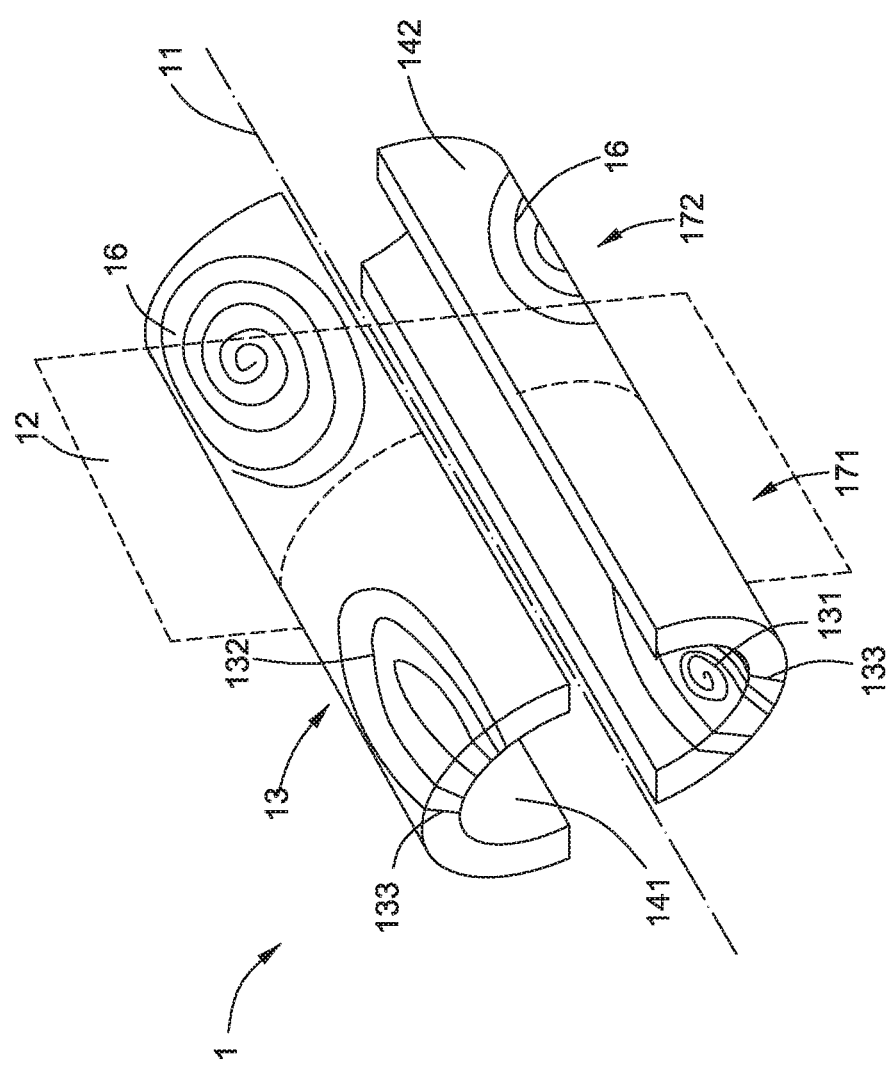
FIG. 2 is a sketch view of the gradient coil unit including a folded coil in accordance with another exemplary embodiment of the present disclosure.

FIG. 2 is a perspective view of another exemplary gradient coil unit, which is separated into two parts for clarity. As shown in FIG. 2, the gradient coil unit 1 comprises at least one folded coil 13 and at least one unfolded coil 16, wherein the at least one folded coil 13 is located at the first side 171 and the at least one unfolded coil 16 is located at the second side 172. Specifically, the gradient coil unit 1 is symmetric about the magnetic gradient axis 11 and comprises two folded coils 13 located at the first side 171 and four unfolded coils 16 located at the second side 172, wherein two of the unfolded coils are not shown in FIG. 2. Each of the unfolded coils 16 comprises a spiral of conductors in a shape of finger print disposed on the first curved surface 141 or the second curved surface 142. In the illustrated embodiment, two of the unfolded coils 16 are disposed on the second curved surface 142, and the other two are disposed on the first curved surface 141 which are not shown in FIG. 2.

Figure 4:
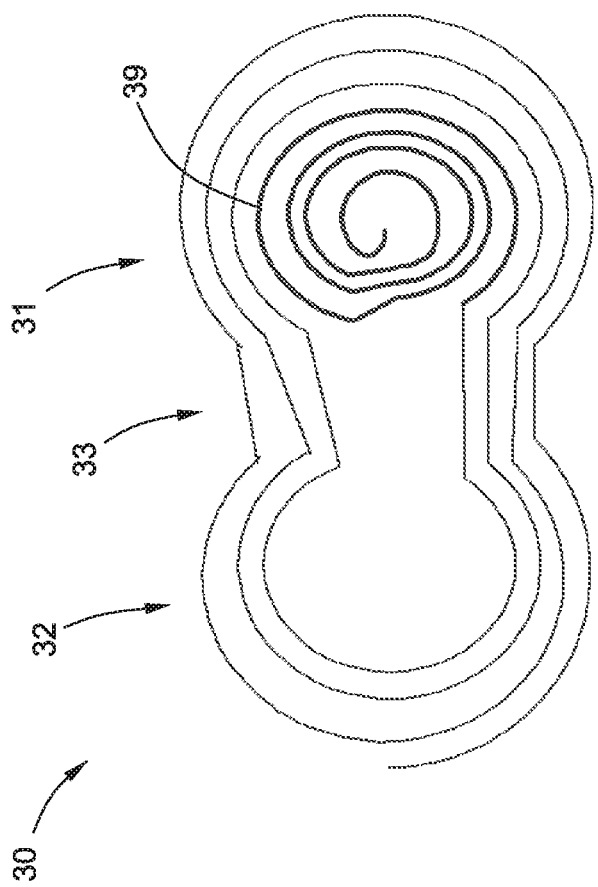
FIG. 4 shows an unfolded status of an exemplary folded coil for gradient coil units of the present disclosure.

In some embodiments, the folded coil used in the embodiments of the present disclosure may be partially made of a hollow wire. FIG. 4 shows an exemplary folded coil 30 partially made of the hollow wire. In order to show the entire folded coil 30 more clearly, an unfolded status of the folded coil 30 is illustrated in FIG. 4. Referring to FIG. 4, the folded coil 30 comprises a first set of curved conductors 31, a second set of curved conductors 32, and a set of connecting conductors 33, wherein a part 39 of the folded coil 30 is made of the hollow wire. The hollow wire has better heat dispersion than a solid wire and thus can improve heat dispersion of the whole gradient coil unit. However, the hollow wire has more complex soldering process, especially at bended parts of the folded coil. If the set of connecting conductors is made of the hollow wire, the manufacturing complexity will be greatly increased. Therefore, in the embodiment shown in FIG. 4, at least a part of the first and second sets of curved conductors 31, 32 is made of the hollow wire, and the set of connecting conductors 33 is made of the solid wire.

More specifically, either of the first and second sets of curved conductors comprises at least one complete conductor loop made of the hollow wire, and the first and second sets of curved conductors other than the at least one complete conductor loop are made of the solid wire, wherein the complete conductor loop refers to a continuous curved conductor in a spiral 360-degree surrounding a center of the spiral.

Figure 5:
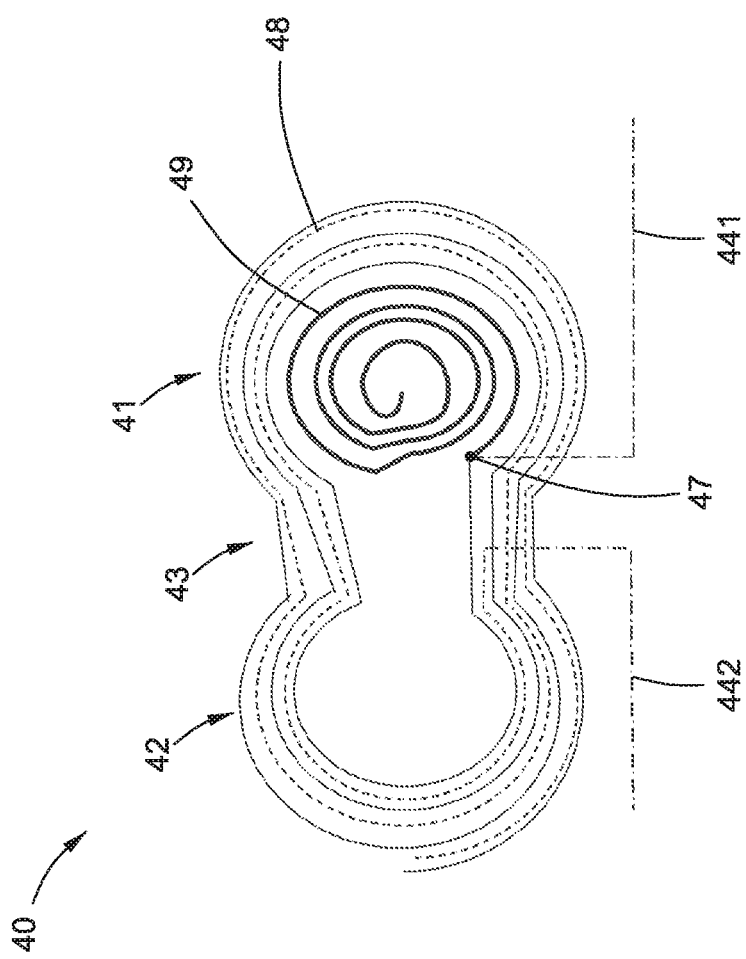
FIG. 5 shows an unfolded status of an exemplary folded coil for gradient coil units of the present disclosure.

As shown in FIG. 5, a folded coil 40 comprises a first set of curved conductors 41, a second set of curved conductors 42, and a set of connecting conductors 43, wherein the first set of curved conductors 41 comprises a plurality of complete conductor loops 49 which is made of a hollow wire, and the rest of the folded coil 40 is made of a solid wire. As such, the hollow wire doesn't fold, and there is only one soldering point 47 between the hollow wire and the solid wire, which not only improves the heat dispersion but also decreases manufacturing complexity. Usually, coolant is passed through the hollow wire for taking away more heat. Therefore, in some embodiments, the folded coil 40 may further comprise a first feed line 441 connected with the hollow wire, configured for feeding the coolant to the hollow wire.

In some embodiments, the folded coil 40 may further comprise a cooling channel 48 disposed side by side with the solid wire for cooling the solid wire, so as to improve the heat dispersion of solid wire part. Usually, coolant is passed through the cooling channel 48 for taking away more heat. Therefore, the folded coil 40 may further comprise a second feed line 442 connected with the cooling channel 48, configured for feeding the coolant to the cooling channel 48.

Figure 6:
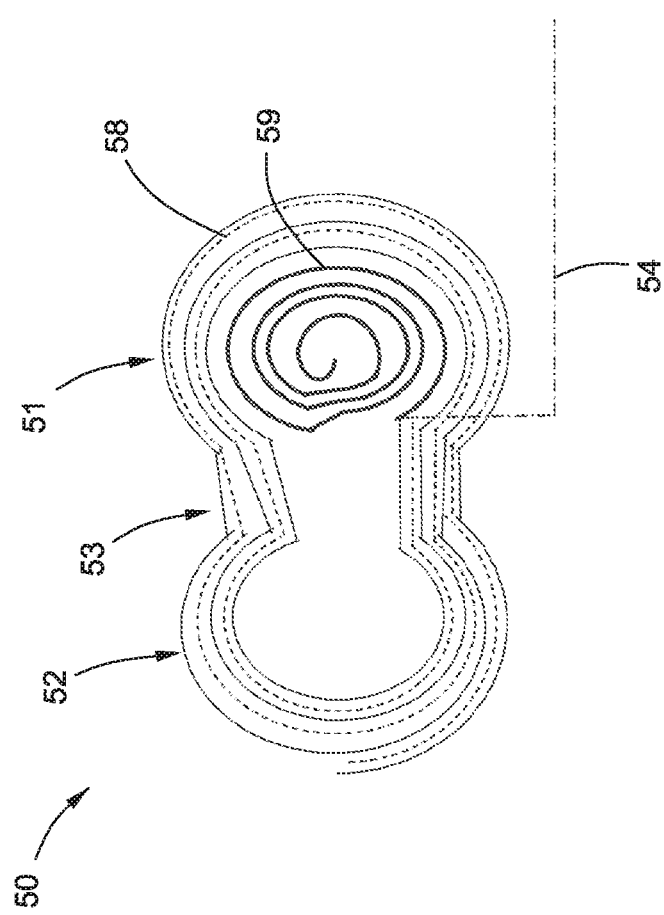
FIG. 6 shows an unfolded status of an exemplary folded coil for gradient coil units of the present disclosure.

In some embodiments, the hollow wire and the cooling channel may share a same feed line, as shown in FIG. 6. Referring to FIG. 6, a folded coil 50 comprises a part 59 made of a hollow wire, and the other part of the folded coil 50 is made of a solid wire. A cooling channel 58 is disposed side by side with the solid wire. The folded coil 50 further comprises a third feed line 54 connected with the cooling channel 58 and the part 59 made of the hollow wire, configured for feeding the coolant.

Figure 7:
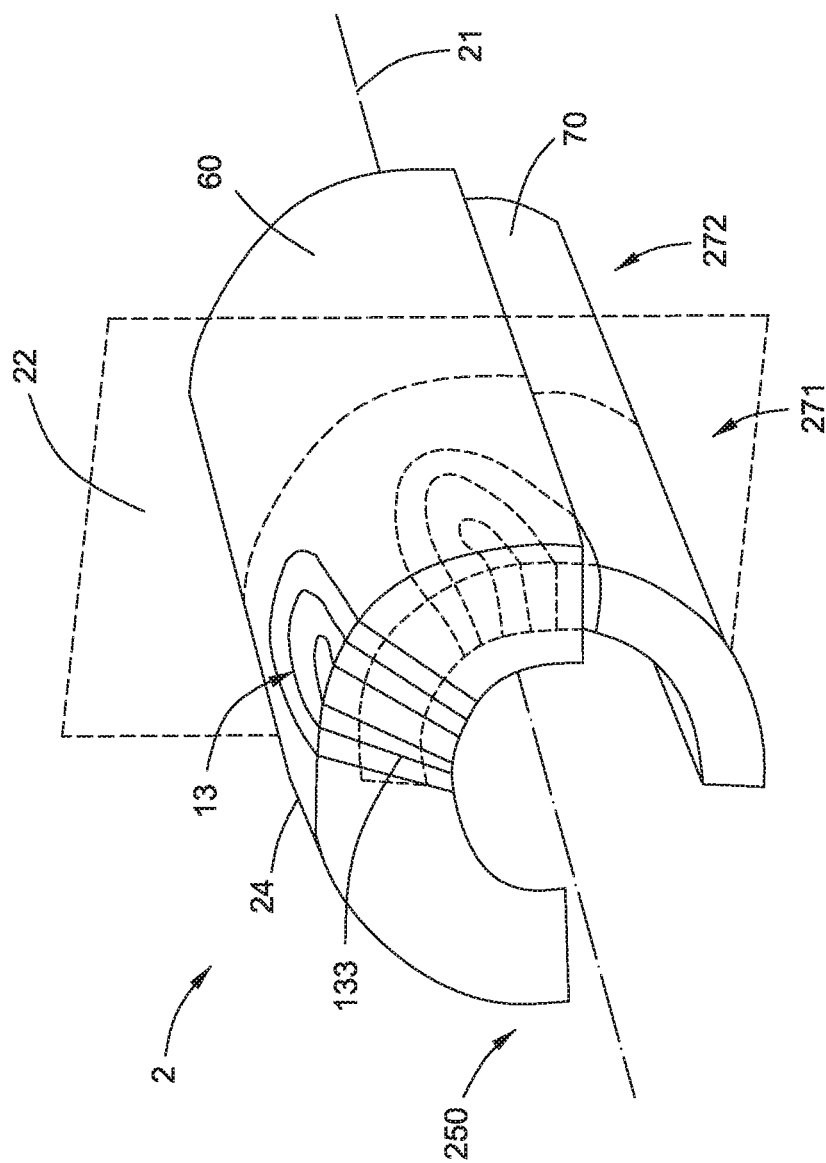
FIG. 7 is a sketch view of an apparatus including an X gradient coil unit and a Y gradient coil unit, with some parts omitted for clarity.

Embodiments of the present disclosure further refer to an apparatus comprising two gradient coil units described above, which is configured to generate two gradient magnetic fields. FIG. 7 is a sketch view of the apparatus in accordance with an exemplary embodiment of the present disclosure, wherein some parts are omitted for clarity. Referring to FIG. 7, an apparatus 2 has a peripheral surface 24 enclosing a magnetic gradient axis 21. A middle plane 22 substantially perpendicular to the magnetic gradient axis 21 at a middle portion of the apparatus 2 divides the apparatus 2 into two side parts, a first side 271 and a second side 272. The apparatus 2 comprises two gradient coil units, denoted as an X gradient coil unit 60 and a Y gradient coil unit 70. It is worth to note that a half of each gradient coil unit is omitted for clarity in FIG. 7. The Y gradient coil unit 70 is substantially concentric with the X gradient coil unit 60, and at least a part of the Y gradient coil unit 70 is sleeved by the X gradient coil unit 60, wherein each of the X and Y gradient coil unit comprises at least one folded coil 13, and the set of connecting conductors 133 of each folded coils is located at the first side 271.

In some embodiments, the apparatus 2 comprises a plurality of folded coils 13, wherein the sets of connecting conductors 133 are all located at the first side 271. As such, the apparatus 2 folds only at the first side 271 but not at the second side 272. This design not only shortens the length of the apparatus 2 in some degrees but also decreases the manufacturing complexity.

FIGS. 8-13 show relationships between the X and Y gradient coil units in accordance with different exemplary embodiments of the present disclosure. As the apparatus has a symmetrical structure about the magnetic gradient axis 21, only a half of the apparatus is illustrated in each of the figures for the purposes of simplification.

Referring to FIGS. 7-8, the X gradient coil unit 60 sleeves the Y gradient coil unit 70. The X gradient coil unit 60 comprises two X folded coils 63 extending across the middle plane 22 from the first side 271 to the second side 272, wherein only one X folded coil 63 is shown in FIG. 8 for clarity. The Y gradient coil unit 70 comprises two Y folded coils 73 extending across the middle plane 22 from the first side 271 to the second side 272, wherein only one Y folded coil 73 is shown in FIG. 8 for clarity. The X folded coil 63 comprises an X first set of curved conductors 631, an X second set of curved conductors 632 and an X set of connecting conductors 633. The Y folded coil 73 comprises a Y first set of curved conductors 731, a Y second set of curved conductors 732 and a Y set of connecting conductors 733. The X first set of curved conductors 631 is closer to the magnetic gradient axis 21 than the Y first set of curved conductors 731. The Y second set of the curved conductors 732 is closer to the magnetic gradient axis 21 than the X second set of curved conductors 632. All of the X and Y sets of connecting conductors 633, 733 are close to a first end 250 of the apparatus 2.

Figure 14:
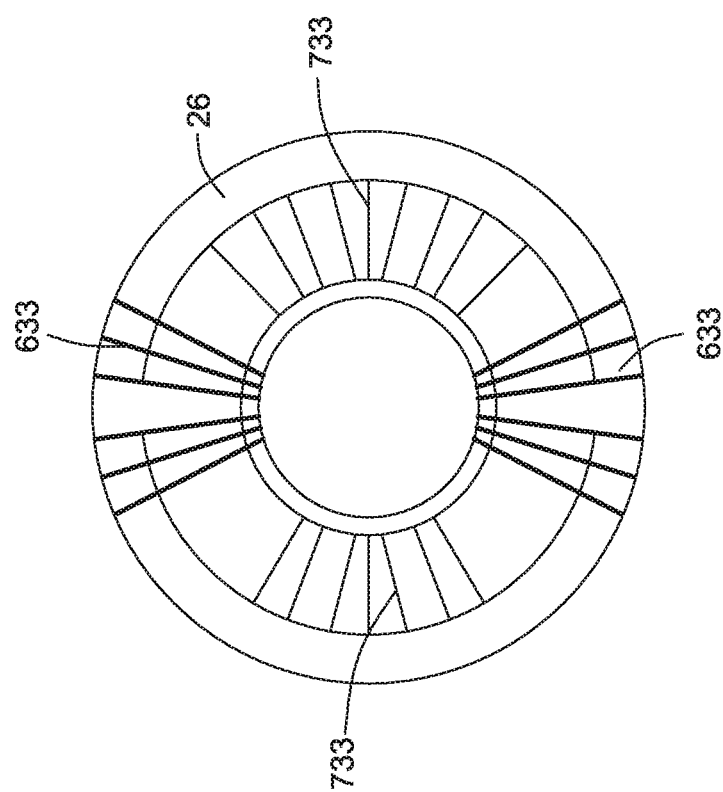
FIG. 14 is a left view of the apparatus in accordance with the exemplary embodiment shown in FIG. 9 or FIG. 11.

In some embodiments, referring to FIG. 9 and FIG. 14, the X and Y sets of connecting conductors 633, 733 are arranged on a same ring surface 26 close to the first end 250 of the apparatus, which further shortens the length of the apparatus.

Referring to FIGS. 7 and 10, the X gradient coil unit 60 sleeves the Y gradient coil unit 70. The X gradient coil unit 60 comprises two X folded coils 63 positioned at the first side 271 and four unfolded coils 66 positioned at the second side 272. The Y gradient coil unit 70 comprises two Y folded coils 73 positioned at the first side 271 and four Y unfolded coils 76 positioned at the second side 272. The X first set of curved conductors 631 is closer to the magnetic gradient axis 21 than the Y first set of curved conductors 731. The Y second set of the curved conductors 732 is closer to the magnetic gradient axis 21 than the X second set of curved conductors 632. All of the X and Y sets of connecting conductors 633, 733 are close to the first end 250 of the apparatus 2.

In some embodiments, referring to FIG. 11 and FIG. 14, the sets of connecting conductors 633, 733 are on a same ring surface 26 close to the first end 250, which further shortens the length of the apparatus 2.

In some embodiments, referring to FIG. 12, the X sets of connecting conductors 633 are close to the first end 250, and the Y sets of connecting conductors 733 are close to the middle plane 22.

Referring to FIG. 7 and FIG. 13, the X gradient coil unit 60 comprises two X folded coils 63 positioned at the first side 271 and four unfolded coils 66 positioned at the second side 272. The Y gradient coil unit 70 comprises two Y folded coils 73 positioned at the first side 271 and four Y unfolded coils 76 positioned at the second side 272. The Y first set of curved conductors 731 is closer to the magnetic gradient axis 21 than the X first set of curved conductors 631. The Y second set of the curved conductors 732 is closer to the magnetic gradient axis 21 than the X second set of curved conductors 632. The X sets of connecting conductors 633 are close to the first end 250 of the apparatus 2, and the Y sets of connecting conductors 733 are close to the middle plane 22.

Figure 15:
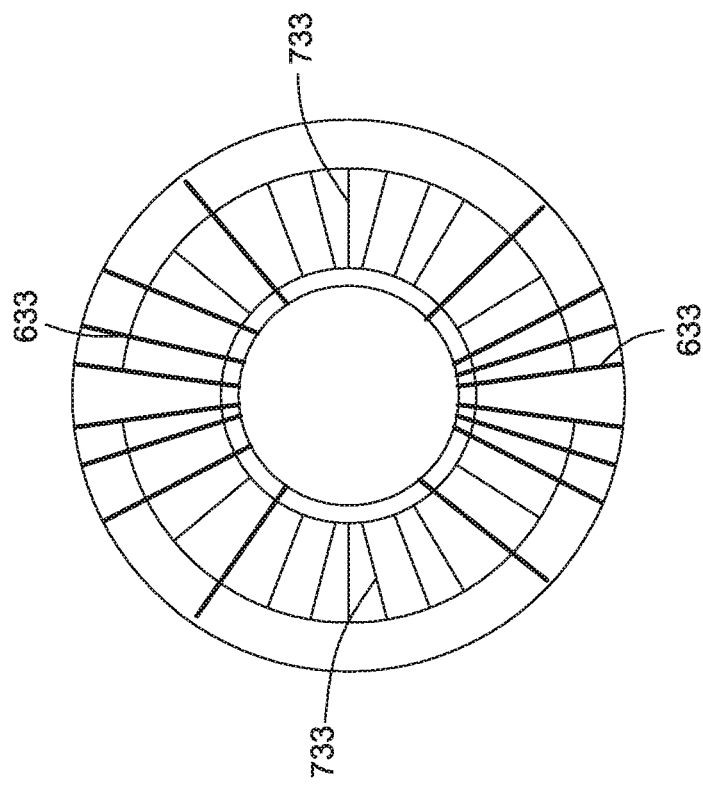
FIG. 15 is a left view of the apparatus in accordance with the exemplary embodiment shown in FIG. 9 or FIG. 11.

FIG. 14 and FIG. 15 are left views of the apparatus in accordance with the exemplary embodiments shown in FIG. 9 or FIG. 11. In these embodiments, the sets of connecting conductors 633, 733 are on the same ring surface 26, but the connecting conductors are not allowed to intersect with each other. Referring to FIG. 14, areas where the X and Y sets of connecting conductors 633, 733 are located don't overlap with each other. Referring to FIG. 15, the areas where the X and Y sets of connecting conductors 633, 733 are located partially overlap with each other, but the connecting conductors don't intersect with each other.

In some embodiments, a patient enters into the MRI system from the first side 271, which has a shorter length and higher openness and serves as a patient side. Compared with a conventional MRI system, a field of view (FOV) of the MRI system in accordance with the embodiments of the present invention is closer to the first end, in such a manner that the target body part of the patient can reach the FOV more easily. Accordingly, the second side 172 which may have more space for other elements such as cooling channels serves as a service side.

In some embodiments, a structure of a first end surface at the patient side is improved to further increase the openness of the patient side. FIGS. 16-17 shows two exemplary structures of the first end surface. Referring to FIG. 16, a distance in an axial direction between the first end surface 251 and the middle plane 22 decreases with getting close to the magnetic gradient axis 21, which increases the openness of the MRI system, so as to reduce anxiety of claustrophobia patients and add more comfort for them. The X and Y folded coils 63, 73 have shapes matching with the first end surface 251.

Referring to FIG. 17, the first end surface comprises a first ring surface 252 and a second ring surface 254 inside and concentric with the first ring surface 252. A distance in the axial direction between the first ring surface 252 and the middle plane 22 is larger than a distance in the axial direction between the second ring surface 254 and the middle plane 22. The X and Y gradient folded coils 63, 73 have shapes matching with the first end surface 251. This design could be applied in a head MRI system. An area 8 shown in FIG. 17 may receive shoulders of a patient, in such a manner that the patient's head can reach the FOV more easily without increasing a diameter of the MRI system, which greatly saves materials and reduces costs.

As will be understood by those familiar with the art, the present disclosure may be embodied in other specific forms without depending from the spirit or essential characteristics thereof. Accordingly, the disclosures and descriptions herein are intended to be illustrative, but not limiting, of the scope of the disclosure which is set forth in the following claims.

We claim:

1. A gradient coil unit having a peripheral surface enclosing a magnetic gradient axis, and a middle plane substantially perpendicular to the magnetic gradient axis at a middle portion of the gradient coil unit, the gradient coil unit comprising at least one folded coil which comprises:
   a first set of curved conductors disposed on a first curved surface;
   a second set of curved conductors disposed on a second curved surface outside the first curved surface and substantially overlapping the first set of curved conductors; and
   a set of connecting conductors connecting selected curved conductors in the first set with selected curved conductors in the second set;
   wherein the at least one folded coil extends across the middle plane from a first side to a second side of the middle plane opposite to the first side, and the set of connecting conductors is located at the first side of the middle plane.

2. The gradient coil unit according to claim 1, comprising a plurality of folded coils, wherein the sets of connecting conductors are all located at the first side of the middle plane.

3. The gradient coil unit according to claim 1, wherein a part of the folded coil is made of a hollow wire.

4. The gradient coil unit according to claim 1, wherein at least a part of the first and second sets of curved conductors is made of a hollow wire, and the set of connecting conductors is made of solid wires.

5. The gradient coil unit according to claim 4, wherein the folded coil further comprises a cooling channel disposed side by side with the solid wire.

6. The gradient coil unit according to claim 5, wherein the folded coil further comprises a feed line connected with the hollow wire and the cooling channel, configured for feeding coolant to the hollow wire and the cooling channel.

7. The gradient coil unit according to claim 1, wherein either of the first and second sets of curved conductors comprises at least one complete conductor loop made of a hollow wire, and the first and second sets of curved conductors other than the at least one complete conductor loop are made of solid wires.

8. A gradient coil unit having a peripheral surface enclosing a magnetic gradient axis, and a middle plane substantially perpendicular to the magnetic gradient axis at a middle portion of the gradient coil unit, the gradient coil unit comprising:
   at least one folded coil which comprises:
      a first set of curved conductors disposed on a first curved surface;
      a second set of curved conductors disposed on a second curved surface outside the first curved surface and substantially overlapping the first set of curved conductors; and
      a set of connecting conductors connecting selected curved conductors in the first set with selected curved conductors in the second set, the set of connecting conductors being located at a first side of the middle plane; and
   at least one unfolded coil, which comprises a spiral of conductors disposed on the first or second curved surface.

9. The gradient coil unit according to claim 8, wherein the at least one folded coil is located at the first side and the at least one unfolded coil is located at a second side of the middle plane opposite to said first side.

10. An apparatus having a peripheral surface enclosing a magnetic gradient axis, and a middle plane substantially perpendicular to the magnetic gradient axis at a middle portion of the apparatus, the apparatus comprising an X gradient coil unit and a Y gradient coil unit substantially concentric with X gradient coil unit and at least a part of which sleeved by the X gradient coil unit, wherein each of the X and Y gradient coil unit comprises at least one folded coil which comprises:
- a first set of curved conductors disposed on a first curved surface;
- a second set of curved conductors disposed on a second curved surface outside the first curved surface and substantially overlapping the first set of curved conductors; and
- a set of connecting conductors connecting selected curved conductors in the first set with selected curved conductors in the second set;
- wherein the at least one folded coil extends across the middle plane from a first side to a second side of the middle plane opposite to the first side, and the set of connecting conductors is located at the first side of the middle plane.

11. The apparatus according to claim 10, comprising a plurality of folded coils.

12. The apparatus according to claim 11, wherein the sets of connecting conductors are all on a same ring surface close to a first end of the apparatus.

13. The apparatus according to claim 10, wherein a distance in an axial direction between a first end surface of the apparatus and the middle plane decreases with getting close to the magnetic gradient axis.

14. The apparatus according to claim 10, wherein a first end surface of the apparatus comprises a first ring surface and a second ring surface inside and concentric with the first ring surface, and a distance in an axial direction between the first ring surface and the middle plane is larger than a distance between the second ring surface and the middle plane.

* * * * *